United States Patent [19]
Konwitz et al.

[11] Patent Number: 5,558,670
[45] Date of Patent: Sep. 24, 1996

[54] HANDPIECE FOR LASER APPARATUS

[75] Inventors: Ellie Konwitz, Ramat Gan, Israel; Yves V. Kamami, Paris, France

[73] Assignee: Laser Industries Ltd., Tel Aviv, Israel

[21] Appl. No.: 255,430

[22] Filed: Jun. 8, 1994

[30] Foreign Application Priority Data

Jun. 8, 1993 [IL] Israel ........................................ 105957

[51] Int. Cl.⁶ .................................................... A61B 17/36
[52] U.S. Cl. .................................. 606/18; 606/13; 606/17
[58] Field of Search ..................................... 606/7, 13–18; 607/88, 89

[56] References Cited

U.S. PATENT DOCUMENTS

| | | | |
|---|---|---|---|
| 3,417,754 | 12/1968 | Smart | 606/18 |
| 3,804,095 | 4/1974 | Bredemeir | 606/18 X |
| 3,906,953 | 9/1975 | Wallace et al. | 606/18 X |
| 4,672,961 | 6/1987 | Davies | 606/18 X |
| 4,760,840 | 8/1988 | Fournier, Jr. et al. | 606/15 |
| 4,913,132 | 4/1990 | Gabriel | 606/17 |
| 5,041,121 | 8/1991 | Wondrazek et al. | 606/15 |
| 5,337,741 | 8/1994 | Diamond | 606/17 X |
| 5,342,358 | 8/1994 | Diakuzono | 606/15 X |

Primary Examiner—Angela D. Sykes
Assistant Examiner—Michael Peffley
Attorney, Agent, or Firm—Ladas & Parry

[57] ABSTRACT

A handpiece for laser apparatus includes a handle having a proximal end connectible to a laser beam source, a distal end through which the laser beam is delivered to a working area, and a passageway connecting the proximal end to the distal end; and a mirror carried at the distal end of the handle and tilted with respect to the longitudinal axis of the passageway to deliver the laser beam to a selected point in the working area. The mirror is elongated along one direction to permit directing the laser beam along a beam axis intercepting the mirror at a first point and reflecting the laser beam to the working area, and to permit viewing the working area along a viewing axis intercepting the mirror at a second point thereof displaced from the first point in the elongated direction.

14 Claims, 2 Drawing Sheets

HANDPIECE FOR LASER APPARATUS

FIELD AND BACKGROUND OF THE INVENTION

The present invention relates to a handpiece for laser apparatus. The invention is particularly useful for surgical lasers, and is therefore described below with respect to this application.

Surgical lasers, particularly $CO_2$ lasers, are presently used for cutting or ablating tissues in various confined body cavities. One recently-developed application of lasers is in the treatment of snoring. A common cause of snoring is a long uvula (the small, conical, fleshy mass of tissue suspended from the center of the soft pallet above the back of the tongue) and redundant soft pallet that vibrates during respiration. Occasionally, snoring is accompanied by an enlargement of the tonsils. In the surgical treatment of snoring, the surgeon performs a vertical resection of the soft pallet on both sides of the uvula, sparing the uvula itself, with further ablation with the laser of the lateral and inferior sides of the uvula to create a "new uvula" that is higher and smaller. Surgical lasers are also used for reshaping or removing the tonsils (tonsillectomy), and for removing or reshaping posterior parts of the tongue (glosectomy).

Such applications of surgical lasers involve a number of troublesome problems. One problem is to provide clear viewing of the working area by the surgeon. Another problem is to protect sensitive tissue in this area from undue heat or from exposure to the laser beam. Further problems are to evacuate the vaporized tissue and to prevent contamination of the lens included in such apparatus for focussing or defocussing the laser beam on the working area. While the foregoing problems are particularly troublesome with respect to the above-described applications for surgical lasers, they are also present to some degree in many other applications of surgical lasers.

OBJECTS AND BRIEF SUMMARY OF THE INVENTION

An object of the present invention is to provide laser apparatus, and particularly a handpiece for laser apparatus, eliminating or reducing the foregoing problems in the use of surgical lasers.

According to one aspect of the present invention, there is provided a handpiece for laser apparatus, comprising: a handle having a proximal end connectible to a laser beam source, a distal end through which the laser beam is delivered to a working area, and a passageway connecting the proximal end to the distal end; and a mirror carried at the distal end of the handle and tilted with respect to the longitudinal axis of the passageway to deliver the laser beam to a selected point in the working area. The mirror is elongated in one direction such as to permit directing the laser beam along a beam axis which impinges the mirror at a first point thereof and reflects the laser beam to the working area, and also to permit viewing the working area along a viewing axis which extends externally of the handle, which is devoid of any optical elements to the mirror, and which impinges the mirror at a second point thereof displaced from the first point in the elongated direction.

According to further features in the described preferred embodiment, the mirror is mounted in a metal mirror holder and is to be thermally insulated therefrom except for a thermally-conductive link conducting the heat from the mirror to the handle and substantially thermally insulating the remainder of the holder from the mirror. More particularly, in the described preferred embodiment, the mirror holder is thermally insulated from the mirror by an airgap, and the thermally-conductive link is a threaded fastener mounting the mirror to the mirror holder.

According to still further features in the described preferred embodiment, the mirror has a reflecting surface which is slightly absorptive, sufficiently to heat the surface of the mirror such as to vaporize any moisture tending to condense thereon. Preferably, the mirror is of polished stainless steel.

According to still further features in the described preferred embodiment, the mirror is carried by a stem which is flattened at the distal end to facilitate viewing the working area along the viewing axis. More particularly, the stem is of cylindrical configuration and is flattened at the distal end to form a flattened surface increasing in width towards the distal end.

According to still further features in the described preferred embodiment, the proximal end of the handle includes a fitting having a lens for focussing or defocussing the laser beam, and a gas inlet adjacent to the lens on the side thereof facing the distal end of the handle for producing a flow of gas across the face of the lens in order to prevent contamination thereof. In addition, the fitting further includes a suction outlet between the gas inlet and the distal end of the handle for evacuating the material at the working area vaporized by the laser beam.

As described, the mirror is carried by an end unit attachable to and detachable from the distal end of the handle. The apparatus further includes a backstop end unit attachable to and detachable from the distal end of the handle in place of the mirror end unit, the backstop end unit being non-transmission of laser radiation to block the laser beam exiting from the distal end of the handle behind the working area so as to protect tissue behind the working area.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
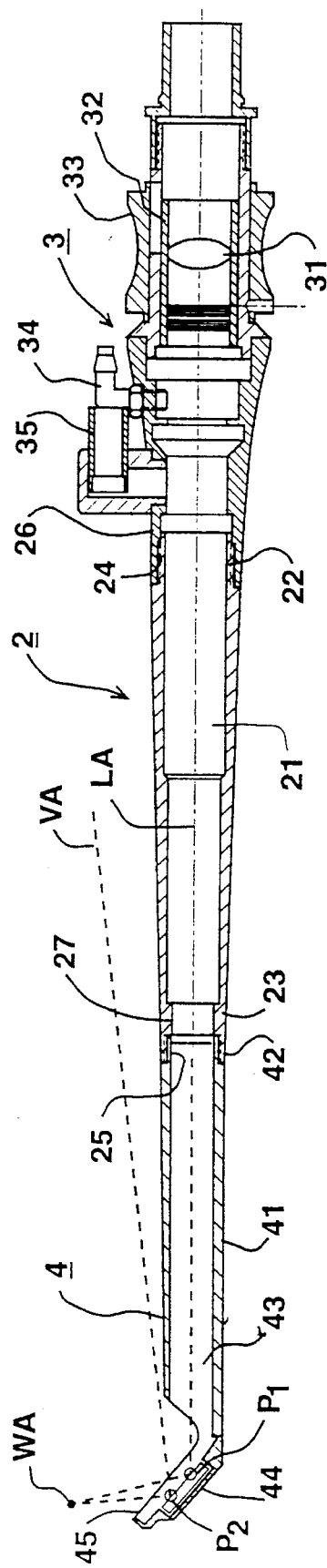
FIG. 1 is a longitudinal sectional view illustrating one form of handpiece constructed in accordance with the present invention.

The handpiece illustrated in FIG. 1 comprises a handle, generally designated 2, to be grasped by the surgeon; a fitting, generally designated 3, coupled to the proximal end of the handle 2 and in turn adapted to be coupled to a laser beam source, such as the articulated arm of a surgical laser; and a mirror end unit 4 at the distal end of handle 2 for reflecting the laser beam to the working area, indicated in FIG. 1 as point WA. As will be described more particularly below, the illustrated handpiece is constructed to direct the laser beam along the laser axis LA shown in FIG. 1 to a working area WA, and also to permit the surgeon holding the handpiece to view the working area WA along the viewing axis VA.

The handle 2 is of hollow construction so as to define a longitudinally-extending passageway 21 from its proximal end 22 connected to fitting 3, to its distal end 23 connected to the mirror end unit 4. The proximal end 22 of handle 2 may thus be externally threaded, as shown at 24, for coupling to fitting 3, and the distal end of the handle may be internally threaded, as shown at 25, for coupling to the mirror end unit 4. Both ends of the handle may be provided with sealing rings, as shown at 26 and 27, respectively. Handle 2 is preferably tapered slightly, being of larger diameter at its proximal end 22 and uniformly decreasing slightly in diameter towards its distal end 23.

Fitting 3 connected to the proximal end 22 of handle 2 carries a lens 31 mounted in a holder 32. Holder 32 may be moved axially by button 33 to focus or defocus the laser beam with respect to the working area WA. Fitting 3 further includes a nipple 34, adjacent to lens 31 on the side thereof facing the mirror end unit 4, for inletting a gas in order to prevent the accumulation of contamination on lens 31 during the operation of the laser. Fitting 3 includes a second nipple 35, between nipple 34 and the mirror end unit 3. Nipple 35 is connectible to a source of suction and thereby serves as a suction outlet for evacuating, via the mirror end unit 4 and passageway 21 of handle 2, the material vaporized by the laser beam.

Figure 2:
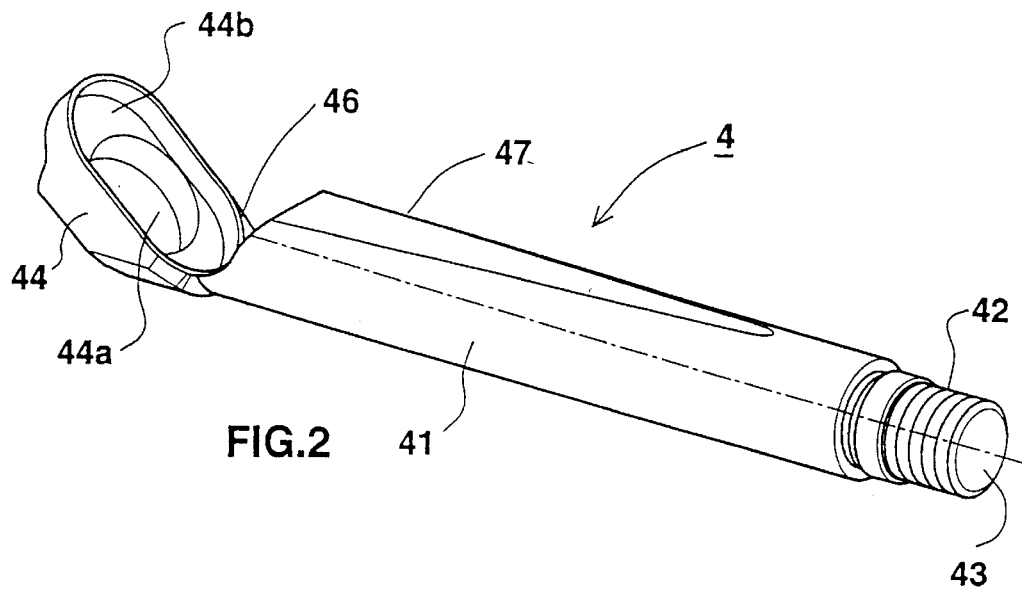
FIG. 2 is a three-dimensional view illustrating the mirror end unit of the handpiece of FIG. 1 with the mirror removed.

The mirror end unit 4 is more particularly illustrated in FIG. 2. It includes a stem 41 formed with external threads 42 at one end and with a longitudinally-extending passageway 43 for conducting the laser beam from the handle 2 to a mirror 45 mounted within a holder 44 carried at the opposite end of stem 41. Mirror holder 44 is tilted with respect to the longitudinal axis of passageway 42 through stem 41 and passageway 21 through handle 2.

As shown particularly in FIG. 2, stem 41 is of cylindrical configuration, but its distal end adjacent to mirror holder 44 is cut at a bias to define an angular end face 46 facing mirror 45. In addition, the surface of stem 41 is flattened, as shown at 47, starting from a point adjacent its threaded end 42 to be coupled to handle 2, and increasing in width to the angular end face 46.

Figure 4:
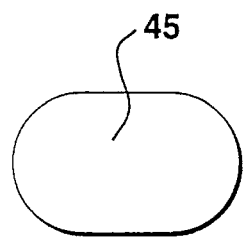
FIG. 4 is a plan view of the mirror of FIG. 3.

Holder 44 of the mirror unit 4 is of metal and is integrally formed with its stem 41 to extend at an angle to the longitudinal axis of the stem. Mirror 45 is of oblong configuration, being elongated in the direction of the longitudinal axis of the mirror unit 4. As shown in FIG. 4, two of its opposed sides are straight and parallel to each other, whereas the other two opposed sides are of semi-circular configuration. The mirror is preferably made of stainless steel which has been polished to reflect the beam impinging it, but to be sufficiently absorptive of the beam so as to generate enough heat to vaporize any moisture condensing on the face of the mirror. Such a construction thereby prevents fogging of the mirror when the handpiece is inserted into the mouth of a subject for performing one of the surgical procedures described earlier.

Figure 3:
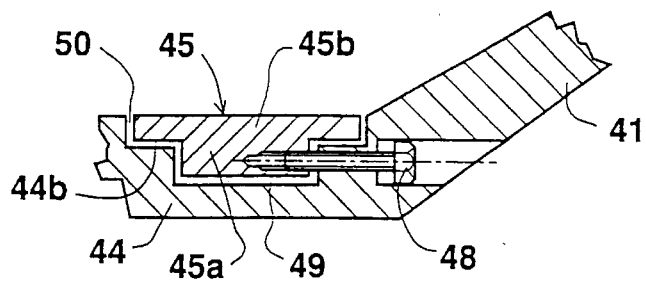
FIG. 3 is a sectional view illustrating the construction of the mirror end unit.

As shown in FIG. 3, mirror 45 is integrally formed with an inner section 45a received within the inner cavity section 44a of the holder 44, and with an outer section 45b received within the outer cavity section 44b of the holder. The mirror is secured within the holder by a metal threaded fastener 48 passing through the holder 44 and received within a threaded opening 49 formed in the inner mirror section 45a.

As also seen in FIG. 3, mirror 45 is thermally insulated from the metal holder 44 by an airgap, shown at 50, for the complete surface of the mirror facing the holder except for threaded fastener 48. Fastener 48, being of metal, thereby serves as a thermally-conductive link conducting the heat from the mirror to the metal holder 44, and from there to stem 41 of the mirror unit 4.

Thus, the external surface of the metal holder 44, which may contact sensitive parts of the subject's mouth or throat, is maintained relatively cool so as not to irritate or damage the tissue it contacts. On the other hand, the heat generated by the laser beam is conducted via the thermally-conductive link defined by threaded fastener 48 to stem 41 which serves as a heat sink for dissipating the heat.

The manner of using the handpiece illustrated in FIGS. 1–5 will be apparent from the above description. Thus, fitting 3 connected to the proximal end 22 of handle 2 is coupled to the laser beam source (e.g., the end of the articulated arm in this type of surgical laser), whereas the mirror unit 4 is attached to the distal end of handle 2. The surgeon, grasping handle 2, inserts the mirror unit into the subject's mouth and locates it at the precise position to receive the laser beam, by viewing the working area WA via the viewing axis VA (FIG. 1). Where the laser apparatus is of the type which includes a visible aiming beam (e.g., produced by a helium-neon laser), the surgeon can see precisely the spot of impingement of the working laser beam (e.g., from a $CO_2$ laser) by viewing the visible laser beam spot along the viewing axis VA. After the handpiece has been precisely located, the working laser is energized to produce the laser beam which is reflected from mirror 45 to the working area WA.

As shown in FIG. 1, the elongation of mirror 45 in the direction of the longitudinal axis of the mirror unit 4 permits directing the laser beam along the beam axis LA to intercept the mirror 45 at a first point $P_1$ and to reflect the beam to the working area WA, and at the same time permits viewing the working area WA along a viewing axis VA intercepting the mirror 45 at a second point $P_2$ displaced from the first point $P_1$ in the direction of elongation of the mirror. This permits the surgeon to clearly view the working area before and at the time of operating the laser. This viewing of the working area is further enhanced by the flattened portion 47 and the inclined end surface 46 of the mirror unit stem 41.

Before the working laser beam is energized, pressurized gas (e.g., air) is circulated from inlet 34 across the face of the focussing/defocussing lens 31 in order to prevent contamination of the respective face of the lens. In addition, the suction outlet 35 is connected to a source of suction for evacuating the material at the working area WA vaporized by the laser beam when the laser is energized.

It will be seen that the construction of the handpiece illustrated in the drawings facilitates the viewing of the working area by the surgeon. In addition, the airgap 50 maintains the external surfaces of the mirror holder 44 relatively cool during the operation of the laser, while the heat is conducted away from the mirror via the metal fastener 48 which serves as a thermally-conductive link to the stem section 41 of the mirror unit 4, thereby avoiding irritating or damaging tissue contacted by the outer surface of the mirror holder. Further, the flow of gas via the inlet 34 across the lens 31 prevents fogging of the lens; and the connection of nipple 35 to a vacuum source evacuates the material at the working area vaporized by the laser beam.

All the foregoing features make the illustrated handpiece particularly useful in the above-described surgical applications for treating a subject for snoring, for reshaping or removing the tonsils, or for reshaping or removing portions of the posterior part of the tongue.

The mirror unit 4 can be supplied in the form of a plurality of interchangeable units each including a mirror holder 44 at a different angle to the longitudinal axis of the stem 41, according to the particular application. Alternatively, the mirror holder 44 could be adjustably mounted to the stem 41 to permit adjusting the tilt axis of the mirror.

Figure 5:
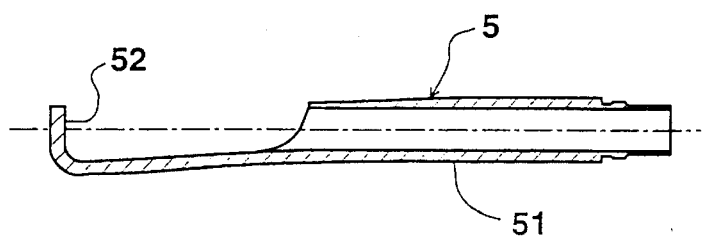
FIG. 5 illustrates a backstop end unit which may also be used in lieu of the mirror end unit in the handpiece of FIG. 1.

Among the interchangeable units that could be supplied is the backstop end unit 5 illustrated in FIG. 5. This unit also includes a stem 51 quickly attachable and removable from the handle 2, and a backstop 52 of a material which is non-transmissive of solar radiation, to be located behind the tissue to be subjected to the laser beam in order to block the laser radiation and thereby to protect other tissue from such radiation.

While the invention has been described with respect to one preferred embodiment, it will be appreciated that many variations, modifications and other applications of the invention may be made.

What is claimed is:

1. A handpiece for laser apparatus, comprising:
    a handle having a proximal end connectible to a laser beam source, a distal end through which the laser beam is delivered to a working area, and a passageway connecting said proximal end to said distal end;
    and a mirror carried at said distal end of the handle and tilted with respect to the longitudinal axis of said passageway to deliver said laser beam to a selected point in the working area;
    said mirror being elongated in one direction to permit directing the laser beam along a beam axis which impinges the mirror at a first point thereof and reflects the laser beam to the working area, and also to permit viewing said working area along a viewing axis which extends externally of the handle, which is devoid of any optical elements to said mirror, and which impinges said mirror at a second point thereof displaced from said first point in said elongated direction;
    said mirror being mounted in a metal mirror holder and being thermally insulated therefrom except for a thermally-conductive link conducting the heat from the mirror to said handle and substantially thermally insulating the remainder of the holder from the mirror.

2. The handpiece according to claim 1, wherein said mirror holder is thermally insulated from the mirror by an airgap.

3. The handpiece according to claim 2, wherein said thermally-conductive link is a threaded fastener mounting the mirror to the mirror holder.

4. The handpiece according to claim 1, wherein said mirror has a reflecting surface which is slightly absorptive sufficiently to heat the surface of the mirror such as to vaporize any moisture tending to condense thereon.

5. The handpiece according to claim 4, wherein said mirror is of polished stainless steel.

6. The handpiece according to claim 1, wherein said mirror is carried by a stem which is flattened at said distal end to facilitate viewing the working area along said viewing axis.

7. The handpiece according to claim 6, wherein said stem is of cylindrical configuration and is flattened at said distal end to form a flattened surface increasing in width towards said distal end.

8. The handpiece according to claim 1, wherein said proximal end of the handle includes a fitting having a lens for focussing or defocussing the laser beam, and a gas inlet adjacent to the lens on the side thereof facing said distal end of the handle for producing a flow of gas across the face of the lens in order to prevent contamination thereof.

9. The handpiece according to claim 8, wherein said fitting further includes a suction outlet between said gas inlet and said distal end of the handle for evacuating the material at the working area vaporized by the laser beam.

10. The handpiece according to claim 1, wherein said mirror is carried by a mirror unit attachable to and detachable from the distal end of the handle.

11. The combination of the handpiece according to claim 10, and a backstop end unit attachable to and detachable from the distal end of the handle in place of said mirror end unit, said backstop end unit being non-transmissive of laser radiation to block the laser beam exiting from the distal end of the handle behind the working area so as to protect tissue behind the working area.

12. A handpiece for laser apparatus, comprising:
    a handle having a proximal end connectible to a laser beam source, a distal end through which the laser beam is delivered to a working area, and a passageway connecting said proximal end to said distal end;
    and a mirror carried at said distal end of the handle and tilted with respect to the longitudinal axis of said passageway to deliver said laser beam to a selected point in the working area;
    said mirror being mounted in a metal mirror holder so as to be thermally insulated therefrom except for a thermally-conductive link conducting the heat from the mirror to said handle and substantially thermally insulating the remainder of the holder from the mirror.

13. The handpiece according to claim 12, wherein said mirror is elongated in one direction to permit directing the laser beam along a beam axis which impinges the mirror at a first point thereof and reflects the laser beam to the working area, and to permit viewing said working area along a viewing axis which extends externally of the handle, which is devoid of any optical elements to said mirror, and which impinges said mirror at a second point thereof displaced from said first point in said elongated direction.

14. The handpiece according to claim 12, wherein said mirror holder is thermally insulated from the mirror by an airgap.

* * * * *